United States Patent [19]

Drube

[11] Patent Number: 5,631,245
[45] Date of Patent: May 20, 1997

[54] METHOD FOR MEDICATING THE INFLAMMATORY CONTROLLING SYSTEM AND ADVERSE INFLAMMATORY REACTIONS AND FOR MAKING COMPOUNDS FOR TREATING THE PATHOLOGY OF ADVERSE INFLAMMATORY REACTIONS

[75] Inventor: Clairmont G. Drube, Green Valley, Ariz.

[73] Assignee: Biodynamics Pharmaceuticals, Inc., Green Valley, Ariz.

[21] Appl. No.: 470,501

[22] Filed: Jun. 6, 1995

[51] Int. Cl.$^6$ .................... A01N 43/04; A61K 31/70
[52] U.S. Cl. .................... 514/62; 514/814; 514/826; 514/860; 514/861; 514/863; 514/866; 514/884; 514/885; 514/886; 514/893; 514/912; 514/931; 514/934; 536/18.7; 536/22.1; 536/53
[58] Field of Search ........................ 536/18.7, 22, 53; 514/62, 814, 826, 860, 861, 863, 866, 884, 885, 886, 893, 912, 931, 934

[56] References Cited

U.S. PATENT DOCUMENTS

| | | | |
|---|---|---|---|
| 4,647,453 | 3/1987 | Meisner | 424/54 |
| 4,695,590 | 9/1987 | Lippman | 514/724 |
| 4,737,488 | 4/1988 | Lockhoff et al. | 514/42 |
| 4,772,591 | 9/1988 | Meisner | 514/62 |
| 4,870,061 | 9/1989 | Speck | 514/62 |
| 4,957,906 | 9/1990 | Yoshikumi et al. | 514/42 |
| 5,177,062 | 1/1993 | Miyata et al. | 514/23 |
| 5,219,843 | 6/1993 | Macher | 514/62 |
| 5,248,668 | 9/1993 | Wu | 514/25 |

OTHER PUBLICATIONS

Linek et al., "Structure and Rearrangement Reactions...", *Carbohydrate Research*, vol. 164, 1987, pp. 195–205.

Hodge et al., "Preparation and Properties of Dialditylamines", vol. 28, Oct., 1963, pp. 2784–2788.

Panigot et al., "Reaction of Glycosyl Halides with Benzyl Grignard Reagents: Unexpected o-Tolyl...", *J. Carbohydrate Chemistry*, vol. 13, No. 2, 1994, pp. 293–302.

Tsuchida et al., "Formation of Deoxy-fructosazine...", *Agr. Biol. Chem.*, vol. 37, No. 11, 1973, pp. 2571–2578.

*Primary Examiner*—James O. Wilson
*Attorney, Agent, or Firm*—Shoemaker and Mattare, Ltd.

[57] ABSTRACT

Adverse inflammatory reactions can be treated by administrating to an organism a composition having diglucosylamine as the active ingredient. The preferred compound is di-Beta-D-glucopyranosylamine. A simple method for making diglucosylamine in high purity is obtained by reacting glucose, a nitrogen containing base, and either methanol or ethanol to form the diglucosylamine and then recovering the diglucosylamine preferably with the use of charcoal. The preferred diglucosylamine, di-Beta-D-glucopyranosylamine, has extraordinary anti-inflammatory activity. It can be formulated with a pharmaceutically acceptable carrier to make pharmaceutical compositions which are effective in treating inflammations. This pharmaceutical composition can also be used to treat adverse inflammatory reactions that are the result of the disruptions of a dynamic network of cellular mechanisms in organisms. In addition, application of this composition also serves to reestablish the balance of the cellular defense network in an organism which has its cellular defense network out of balance. In this unbalanced case, the composition serves to treat the pathology of inflammation and activates the inflammatory control system in vivo.

21 Claims, No Drawings

METHOD FOR MEDICATING THE INFLAMMATORY CONTROLLING SYSTEM AND ADVERSE INFLAMMATORY REACTIONS AND FOR MAKING COMPOUNDS FOR TREATING THE PATHOLOGY OF ADVERSE INFLAMMATORY REACTIONS

BACKGROUND OF THE INVENTION

1. Field of the Invention

This invention relates to the use of di-Beta-D-glucopyranosylamine compounds for controlling the inflammatory controlling system and related diseases and to methods for making the compounds.

2. Description of the Previously Published Art

K. Linek et al, in Carbohydrate Research, 164 (1987), pp. 195–205, discuss "Structure and Rearrangement Reactions of Some Diglycosylamines". These glycosylamines are compounds of interest for the enzymology of carbohydrates, since they are considered as active-site-directed, reversible inhibitors of glycosidases. The compound di-Beta-D-glucopyranosylamine was prepared by the transglycosylation from Beta-D-glucopyranosylamine.

This compound has been discovered in my research conducted on Transfer Factors. For a discussion of Transfer Factors, see G. B. Olson and C. G. Drube, "Modulation of Influenza in Mice by Transfer Factor Therapy" in *Journal of Reticuloendothelial Society*, Vol. 24, No. 3, November 1978. The compound was obtained during purification studies on these transfer factors.

This invention is directed to simpler methods of making this compound and to the discovery of unique uses of this material for controlling the inflammatory controlling system.

3. Objects of the Invention

It is an object of this invention to provide a process for making diglucosylamine from glucose.

It is an object of this invention to provide a process for making di-Beta-D-glucopyranosylamine from glucose and especially from D-(+)-Glucose.

It is a further object of this invention to use di-Beta-D-glucopyranosylamine for controlling the inflammatory controlling system.

It is a further object of this invention to use di-Beta-D-glucopyranosylamine for treating adverse immunological reactions.

It is a further object of this invention to use di-Beta-D-glucopyranosylamine for treating adverse neurological reactions.

It is a further object of this invention to use di-Beta-D-glucopyranosylamine for treating adverse endocrine reactions.

It is a further object of this invention to use di-Beta-D-glucopyranosylamine for treating adverse direct physical or chemical injuries.

It is a further object of this invention to use di-Beta-D-glucopyranosylamine for reestablishing the balance of the cellular defense network in an organism which has its cellular defense network out of balance.

It is a further object of this invention to formulate anti-inflammatory pharmaceutical compositions containing di-Beta-D-glucopyranosylamine.

These and further objects of the invention will become apparent as the description of the invention proceeds.

SUMMARY OF THE INVENTION

Adverse inflammatory reactions that are the result of the disruptions of a dynamic network of cellular mechanisms in organisms can be treated by administrating to the organism a composition having diglucosylamine as the active ingredient. The preferred compound is di-Beta-D-glucopyranosylamine. Administration of this same composition also serves to reestablish the balance of the cellular defense network in an organism which has its cellular defense network out of balance. In this case, the composition serves to treat the pathology of inflammation and activates the inflammatory control system in vivo.

A simple method for making diglucosylamine in higher purity has been developed. The method involves reacting glucose, a nitrogen containing base and either methanol or ethanol to form a diglucosylamine and then recovering the diglucosylamine preferably with the use of charcoal.

The anti-inflammatory compound di-Beta-D-glucopyranosylamine can be formulated with a pharmaceutically acceptable carrier to make pharmaceutical compositions which are effective in treating inflammations.

DESCRIPTION OF THE PREFERRED EMBODIMENTS

Diglucosylamine has been isolated from molasses and it has been synthesized from D-(+)-Glucose by two routes forming products designated BD2K1 and BD2K2. These diglucosylamines are referred to herein generally as BD2K and they have almost unbelievable anti-inflammatory powers.

In the field of anti-inflammatory agents, there are several anti-inflammatory agents designed to control specific types of inflammation based on a specific mediator of the inflammatory response. BD2K, on the other hand, acts differently because it modifies a system in vivo that directly treats all excessive types of inflammation, such as contact hypersensitivity. Therefore, the BD2K compound is broad spectrum and not a specific designed anti-inflammatory agent. Because of BD2K's broad spectrum of applications, it promises to be a good product for treating the inflammatory process and restoring to normal inflammation responses. Moreover, the product's dynamic effect lends itself to combination therapy with other drugs increasing their therapeutic index; that is, it requires less of the drug and therefore minimizes their possible toxic effects.

The very significant anti-inflammatory activity suggests that this compound will be especially useful as a part of the treatment of auto-immune diseases where part of the etiology of the disease is inflammation. The BD2K compound can be used in combination with other auto-immune diseases agents to work together to treat the disease. The BD2K compound has very good tolerance to other compounds such that they can be used together and the BD2K compound does not inhibit the activity of the other active compound.

BD2K seems to work on many levels. It is believed that BD2K repairs or supplements the genetic molecules that regulate the inflammatory control system. The inflammatory control system has a very specific biological activity in vivo. This system controls inflammation that compromises many different systems in the organisms; systems like the neurologic, digestive, metabolic, immune and endocrine. Therefore, the specific effect of BD2K on inflammation makes the compound a broad spectrum product for experimental, therapeutic and prophylactic value.

BD2K has multiple applications to most of the same symptoms as does aspirin and probably to more. However, in contrast, BD2K is very effective as a therapeutic agent applied topically without any irritation, and when it is used parentally shows no indication of toxicity. BD2K can be used in combination with other medications. The compound is a specific therapy for the dynamic positive control of inflammation. Not only does it relieve symptoms, it positively contributes to the cure of the disease, without elevating IgE levels in patient sera.

Without being bound to any particular theory or mechanism, it is postulated that the senescence and longevity of organisms depends on a balance between defense mechanisms that favor life span and the defense mechanisms that counteract disease processes. The mechanisms favoring longevity are those that cause damage to macromolecules and other body components that come from both exogenous or endogenous sources.

Ionization radiation, UV radiation, and xenobiotics, including dietary carcinogens, entailing the most common exogenous genotoxic compounds with which the organisms cope with everyday. Body heat, oxygen free radicals, glucose, and other oxidative sugars are representative of the byproducts of a variety of metabolic pathways and represent unavoidable, potentially genotoxic agents.

The endogenous hormones are involved in advanced senescence of cells or pathologies of disease in organisms. Indeed, they are responsible for regulating developmental processes and reproduction, two phenomena that are essential for the full life process.

To maintain a balanced dynamic cellular defense mechanism in organisms, cells throughout the animal kingdom have a variety of cellular defense mechanism. The most important of these systems are:

(1) DNA repair mechanisms;
(2) antioxidant systems, either enzymatic or nonenzymatic;
(3) production of heat shock and other stress proteins;
(4) activation of nuclear enzymes such as poly(ADP-ribose) polymerase (PAD-PRP); and
(5) apoptosis, programmed cell death cellular defense mechanism.

The sharing mechanisms, (1)–(5) above, are interconnected and constitute a network of integrated cellular defense systems that are considered altogether, and not one by one. Apoptosis is considered a very important mechanism in eliminating heavily mutated cells and thus avoid cell transformation.

The efficiency of the cellular defense mechanisms in an organism is essential to correct functioning of the three main systems responsible for the body homeostasis, that is, the immune, the nervous and the endocrine systems. Owing to their strict anatomical and functional connections with a common evolutionary origin, they are considered, on the whole, as an immunoneuroendocrine integrated system.

Potentially exogenous or endogenous agents can cause the inflammatory system of the organism to over or under react which disrupts the dynamic network of the cellular defense mechanism causing trauma or other disease. BD2K is effective in reestablishing the balance of the cellular defense network by treating the pathology of inflammation by activating in vivo the Inflammatory Controlling System, therefore the substance has many therapeutic and prophylactic employments for the prevention and cure of the causes of the imbalance in the inflammatory system. Examples of the applications are arranged in Tables 1–4 in categories corresponding to the anatomical origins; the immune system, the nervous system, the endocrine system and by direct physical or chemical injury.

Table 1 Adverse Immunological Reactions

Herpes I & II
Herpes Zoster (shingles)
Herpetic Conjunctivitis and Keratitis
Genital Herpes
HIV
Viral Hepatitis
Neoplasia, heavily mutated cells
Systemic Lupus Erythematosus
Rheumatoid Arthritis
Scleroderma
Insulin Dependent Diabetes
Non-Insulin Dependent Diabetes
Hypoglycemia
Pernicious Anemia
Crohn's Disease
Autoimmune Diseases of the Liver
Autoimmune Diseases of the Kidney
Multiple Sclerosis and Immune-Mediated Neuropathies
Rheumatic Fever
Myocarditis (Chagas' Disease and Coxsackie Myocarditis)
Pemphigus Vulgaris
Autoimmune Hemolytic Anemia
Idiopathic Thrombocytopenic Purpura
Autoimmune Neutropenia
Sperm and Testicular Autoimmunity
Intradermal infection, with allergic reactions to the infects
Acute and chronic bacterial infections with allergic reactions to infections
Skin contact hypersensitivities
Optic contact hypersensitivities
Leprosy and other Mycobacterium infections
Combination with anti-microbial agents
Asthma
Eczema
Acne
Psoriasis
Topical treatment of chicken pox
Hypertension
Adrenal Autoimmunity
Myasthenia Gravis and Myositis, etc.

Table 2 Adverse Neurological Reactions

Multiple Sclerosis and Immune-Mediated Neuropathies
Nerve tissue repair
Migraine headache
Herpes Zoster (shingles)
Leprosy Table 3 Adverse Endocrine Reactions Insulin Dependent Diabetes
Non-Insulin Dependent Diabetes
Hypoglycemia
Pernicious Anemia
Autoimmune Diseases of the Liver Control glycation in aging tissues Table 4 Adverse Physical and Chemical Injury Cosmetic Surgery, wound healing Surgical therapy, Organ and Tissue transplantation (wound healing)

Insect bites

Burns

The employment of BD2K with known designed therapeutics for specific entities become more efficient with a better therapeutic index. When treating a fungal infection with known antifungal compounds, the fungi is killed in the tissue, the dead fungal particles remain in the organism. The disease state continues because of the immune hypersensitivity to the fungal fragments in situ. Another example is when treating human keratitis with known antiviral agents, the failure of the treatments with antiviral compounds is due to the immune reaction to the residual viral particle in situ. These immune reactions to fungal and viral particles precipitate an inflammatory condition which disrupts the dynamic cellular defense network against diseases and this can compound other diseases in other systems.

The composition can be indicated for a wide variety of organisms. In addition to the beneficial effects on humans, mammals, and fish, the composition with its anti-inflammatory properties can also assist in moderating diseases of plants and controlling the mechanisms of wilting.

The compound is very active topically when applied directly in aqueous solutions on areas of inflammation. Oral treatment is effective when formulated with an extender, capable of protecting the compound so it can pass the acid environment of the stomach into the alkaline milieu of the small bowel. It has been discovered that the compounds are very active in the alkaline environment, particularly above pH 6.8. It appears that the compound immediately combines with a targeted compound in vivo. The new complex is stable and very active in the organism. The attachment of the glucosylamine to the acceptor molecule is either triggering the molecule to be active or rejuvenating a dormant deleted in vivo compound. This new compound in the organism emerges as being very stable. The duration of the biological activity of the new complex compound is extended for a long period of time after a single treatment with a very small amount of material. The duration of activity of the treatment has been seen for at least five years. Its activity is different than that observed with other anti-inflammatory agents, in which the durations of activity are very short.

These compounds have good therapeutic and prophylactic value in treating adverse acute, subacute and chronic inflammation. They can also contribute to the maintenance of a typical healthy inflammatory system, that is responding every second of an organism's existence, where subclinical reactions may or may not be present.

One of the unique properties of this pharmaceutical composition is that although it is an autoimmune response moderator, it has no effect on the IgE response. The composition is a nonsteroidal, broad spectrum agent for the treatment of inflammation.

As indicated earlier, the compound di-Beta-D-glucopyranosylamine can be prepared by transglycosylation from Beta-D-glucopyranosylamine as described by K. Linek et al in "Structure and Rearrangement Reactions of Some Diglycosylamines," *Carbohydrate Research*, 164 (1987), pp. 195–205.

A less complex reaction has been found by which glucose is reacted with a nitrogen containing base in methanol or ethanol, preferably in the anhydrous form, to form a diglucosylamine and then recovering the diglucosylamine. In the early work, molasses was used as the starting material because glucose is one of the simple sugars found in molasses. However, there are many undefined carbohydrates found in molasses. These carbohydrates are by-products of the sugar industry and these by-products in molasses caused difficulties in the preparation and isolation of BD2K.

To avoid these difficulties, the previously used molasses was replaced with an alpha-anomer of D-+-glucose. This permitted the substitution of a pure chemical for the molasses and, by using pure chemicals, the synthesis of BD2K could be controlled and subject to complete quality control. Two different bases have been used. In one procedure, ammonium hydroxide is used and the product is identified as BD2K1. In the other procedure, NaOH was added to $NH_4H_2PO_4$ in water to produce another BD2K product identified as BD2K2. Both products are the same. In this second procedure, the $NH_3^+$ ion of the monobasic ammonium phosphate is replaced with the $Na^+$ ion from sodium hydroxide to form $NaH_2PO_4$. The monobasic sodium phosphate precipitates out of the methanol water solution when the methanol is added in the procedure. The blend is adjusted to have an excess concentration of dissociated ammonium ions with enough hydroxide ions for a pH of about 11.2 for the preferred dimerization, or transglycosylation of the glucose molecule to synthesize the compound.

After reacting the preferred D-(+)-Glucose, an aqueous nitrogen containing base, and either methanol or ethanol to form glucosylamine, then the methanol or ethanol is evaporated off to form an aqueous phase. A charcoal water slurry is added to the mixture with stirring to absorb the diglucosylamine on the charcoal. Next, the charcoal is separated from the water and then the diglucosylamine is recovered from the charcoal.

A preferred recovery procedure to remove the diglucosylamine from the charcoal is to wash the charcoal with water and to elute the diglucosylamine from the charcoal with anhydrous methanol. The methanol effluent is concentrated and the dried methanol residue is dissolved with warm anhydrous methanol. The methanol solution is stirred into acetone to form a participate which is filtered and washed with acetone. The diglucosylamine is recovered and dried to a powder. A further preferred procedure when washing the charcoal water is to continue to wash until the effluent has a negative 274 UV reading.

The pharmaceutical formulations can be made in at least two forms. For topical application, such as for ophthalmic and for skin application, a preferred composition is:

pyrogen free phosphate buffered saline (pH from 6.8 to 7.2)

EDTA 0.01% benzalkonium chloride 0.01% di-Beta-D-glucopyranosylamine 100 mg/ml

The dosage range for daily topical treatments is 20–200 mg/ml. The pH can be from 6.8 and above with the preferred range being from 6.8 to 7.2.

For oral treatment in human or in animal, a preferred composition by weight is:

30% methyl cellulose (1,5000 pfs)[1]

70% di-Beta-D-glucopyranosylamine

[1]. hydroxypropylcellulose (1,500 pfs) can be substituted for the methyl cellulose.

This composition can be blended thoroughly and made into tablets or gelatin capsules of 75–250 mg and the dose range for daily treatment orally is preferably 2.5–100 mg/kg body weight with parental treatment at the same levels. The methyl cellulose serves as a carrier and it serves to protect the diglucosylamine so it can pass through the acid environment of the stomach.

Having described the basic aspects of the invention, the following examples are given to illustrate specific embodiments thereof.

EXAMPLE 1

This example illustrates how BD2K1 can be made from D-(+)-glucose.

One liter of concentrated ammonium hydroxide, 3 liters of methanol and 250 grams of D-(+)-glucose in the alpha anomer form which was obtained from Sigma Chemical Company were combined and stirred for 2 hours at room temperature. The mixture was then refluxed at 65° C. at a pH of 11.2. The mixture was placed in a rotary evaporator and heated at 65° C. to evaporate off the methanol and produce an aqueous phase.

A charcoal slurry made of 200 g Darco 60 charcoal and 1 liter of deionized water was stirred into the aqueous concentrate and stirring was continued for 1 hour at room temperature. The mixture was filtered using a Whatman #1 filter paper to separate out the charcoal. The charcoal adsorbs the reaction product which will hereafter be identified as BD2K1. The BD2K1 adsorbed charcoal was washed with demineralized water until the fluent has a negative 274 UV reading. The washings are discarded. The charcoal was then mixed with 5 liters of anhydrous methanol to elute off the BK2D1. The fluent was monitored in a 274 nm UV light adsorption pattern. The methanol fluent was concentrated in a rotary evaporator at 65° C. This procedure was repeated 3 times by bringing the methanol residues up in anhydrous methanol and concentrate at 65° C. for evaporation of the residual water.

The dried methanol residue was dissolved in warm anhydrous methanol at 50° C. Any remaining particulate was filtered out using an "M" fritted glass filter and the retentate was discarded. The relative density of the methanol solution was adjusted to 0.82. Slowly, the methanol solution was stirred into 6 volumes of acetone at room temperature. A white precipitate was formed which was collected on an "M" fritted glass filter. The retentate was washed with acetone and kept covered with acetone. Air contact was avoided since the precipitate is very hygroscopic. The acetone fluent was discarded. The final retentate was dried with a vacuum and stored in a sealed desiccated container. The final product was analyzed by NMR and found to be di-Beta-D-glucopyranosylamine and the yield was 135 grams.

EXAMPLE 2

This example illustrates how BD2K2 can be made from D-(+)-glucose by replacing the $NH_4OH$ used in Example 1 with $NH_4H_2PO_4$ and NaOH for the required $NH_3^+$ and $OH^-$ ion concentrations.

One liter of water was stirred into 3 liters of methanol. Then, 10 g of sodium hydroxide and 18.75 g of ammonium hydrogen phosphate were separately stirred into the mixture and the pH obtained was greater than 11.2. Next, 250 g of D-(+)-glucose in the alpha anomer form used in Example 1 was combined and stirred for 2 hours at room temperature. The mixture was then refluxed at 65° C. at a pH of 11.2. The mixture was filtered through a Whatman #1 filter paper. The filtrate was saved and the residue was discarded. The filtrate was placed in a rotary evaporator and heated at 65° C. to evaporate off the methanol and produce an aqueous phase.

A charcoal slurry made of 200 g Darco 60 charcoal and 1 liter of deionized water was stirred into the aqueous concentrate and stirring was continued for 1 hour at room temperature. The mixture was filtered using a Whatman #1 filter paper to separate out the charcoal. The charcoal adsorbs the reaction product which will hereafter be identified as BD2K2. The BD2K2 adsorbed charcoal was washed with demineralized water until the fluent has a negative 274 UV reading. The washings are discarded. The charcoal was then mixed with 5 liters of anhydrous methanol to elute off the BK2D1. The fluent was monitored in a 274 nm UV light adsorption pattern. The methanol fluent was concentrated in a rotary evaporator at 65° C. This procedure was repeated 3 times by bringing the methanol residues up in anhydrous methanol and concentrate at 65° C. for evaporation of the residual water.

The dried methanol residue was dissolved in warm anhydrous methanol at 50° C. Any remaining particulate was filtered out using an "M" fritted glass filter and the retentate was discarded. The relative density of the methanol solution was adjusted to 0.82. Slowly, the methanol solution was stirred into 6 volumes of acetone at room temperature. A white precipitate was formed which was collected on an "M" fritted glass filter. The retentate was washed with acetone and kept covered with acetone. Air contact was avoided since the precipitate is very hygroscopic. The acetone fluent was discarded. The final retentate was dried with a vacuum and stored in a sealed desiccated container. The final product was analyzed by NMR and found to be di-Beta-D-glucopyranosylamine and the yield was 135 grams.

It is understood that the foregoing detailed description is given merely by way of illustration and that many variations may be made therein without departing from the spirit of this invention.

What is claimed is:

1. A method for the treatment of a mammal or fish exhibiting an adverse inflammatory response or reaction that are the result of the disruptions of a dynamic network of cellular mechanisms in said mammal or fish, which method comprises administration of a composition comprising diglucosylamine as the active ingredient to said organism in an amount effective to treat the adverse inflammatory response or reaction.

2. A method for the treatment of adverse inflammatory reactions according to claim 1, wherein the diglucosylamine is di-Beta-D-glucopyranosylamine.

3. A method according to claim 1, wherein the inflammatory reaction being treated is a member of the adverse immunological reactions selected from the group consisting of Herpes I & II, Herpes Zoster, Herpetic Conjunctivitis and Keratitis, Genital Herpes, HIV, Viral Hepatitis, Neoplasia, heavily mutated cells, Systemic Lupus Erythematosus, Rheumatoid Arthritis, Scleroderma, Insulin Dependent Diabetes, Non-Insulin Dependent Diabetes, Hypoglycemia, Pernicious Anemia, Crohn's Disease, Autoimmune Diseases of the Liver, Autoimmune Diseases of the Kidney, Multiple Sclerosis and Immune-Mediated Neuropathies, Rheumatic Fever, Myocarditis (Chagas' Disease and Coxsackie Myocarditis), Pemphigus Vulgaris, Autoimmune Hemolytic Anemia, Idiopathic Thrombocytopenic Purpura, Autoimmune Neutropenia, Sperm and Testicular Autoimmunity, Intradermal infection, with allergic reactions to the infects, Acute and chronic bacterial infections with allergic reactions to infections, Skin contact hypersensitivities, Optic contact hypersensitivities, Leprosy and other Mycobacterium infections, Combination with anti-microbial agents, Asthma, Eczema, Acne, Psoriasis, Topical treatment of chicken pox, Hypertension, Adrenal Autoimmunity, and Myasthenia Gravis and Myositis.

4. A method according to claim 1, wherein the inflammatory reaction being treated is a member of the adverse neurological reactions selected from the group consisting of Multiple Sclerosis and Immune-Mediated Neuropathies, Nerve tissue repair, Migraine headache, Herpes Zoster, and Leprosy.

5. A method according to claim 1, wherein the inflammatory reaction being treated is a member of the adverse endocrine reactions selected from the group consisting of Insulin Dependent Diabetes, Non-Insulin Dependent Diabetes, Hypoglycemia, Pernicious Anemia, Autoimmune Diseases of the Liver, and Control glycation in aging tissues.

6. A method according to claim 1, wherein the inflammatory reaction being treated is a member of the adverse direct physical or chemical injuries selected from the group consisting of Cosmetic Surgery, wound healing, Surgical therapy, Organ and Tissue transplantation (wound healing), Insect bites, and Burns.

7. A method according to claim 1, wherein the administration is topically.

8. A method according to claim 1, wherein the administration is orally.

9. A method according to claim 8, wherein the diglucosylamine is formulated with a pharmaceutically acceptable extender to protect the diglucosylamine so it can pass through the acid environment of the stomach.

10. A method according to claim 1, wherein the administration is parentally.

11. A method according to claim 1, wherein the diglucosylamine compound is administered in combination with other auto-immune disease treating agents to augment treatment of said disease.

12. A method for making a diglucosylamine which affects the inflammatory control system comprising the steps of:
   a) reacting glucose, a nitrogen containing base and, methanol or ethanol to form a diglucosylamine; and
   b) recovering the diglucosylamine.

13. A method for making a diglucosylamine which affects the inflammatory control system comprising the steps of:
   a) reacting D-(+)-Glucose, an aqueous nitrogen containing base and either methanol or ethanol to form glucosylamine;
   b) evaporating off the methanol or ethanol to form an aqueous phase;
   c) adding a charcoal water slurry to the mixture with stirring so as to absorb the diglucosylamine on the charcoal;
   d) separating the charcoal from the water; and
   e) recovering the diglucosylamine.

14. A method according to claim 13, wherein the diglucosylamine is di-Beta-D-glucopyranosylamine.

15. A method according to claim 13, wherein the base is ammonium hydroxide.

16. A method according to claim 13, wherein the base is a mixture of ammonium hydrogen phosphate and sodium hydroxide.

17. A method according to claim 13, wherein the charcoal is Darco charcoal.

18. A method according to claim 13, wherein the D-(+)-Glucose is in the alpha anomer form.

19. A method according to claim 13, wherein the methanol or ethanol is in the anhydrous form.

20. A method according to claim 13, wherein the recovery step (e) comprises:
   a) washing the charcoal with water;
   b) eluting the diglucosylamine from the charcoal with anhydrous methanol;
   c) concentrating the methanol effluent;
   d) dissolving the dried methanol residue with warm anhydrous methanol;
   e) stirring the methanol solution into acetone to form a participate which is filtered and washed with acetone; and
   f) recovery and drying the diglucosylamine powder.

21. A method according to claim 13, wherein the charcoal is washed with water until the effluent has a negative 274 UV reading.

* * * * *